United States Patent [19]

Aufdembrink

[11] Patent Number: 5,128,303
[45] Date of Patent: Jul. 7, 1992

[54] LAYERED METAL OXIDES CONTAINING INTERLAYER OXIDES AND THEIR SYNTHESIS

[75] Inventor: Brent A. Aufdembrink, Voorhees, N.J.

[73] Assignee: Mobil Oil Corp., Fairfax, Va.

[21] Appl. No.: 587,481

[22] Filed: Sep. 21, 1990

Related U.S. Application Data

[63] Continuation of Ser. No. 443,071, Oct. 5, 1989, abandoned, which is a continuation of Ser. No. 179,949, filed as PCT/US87/01444, Jun. 11, 1987, abandoned.

[51] Int. Cl.$^5$ .......................... B01J 21/06; B01J 20/10
[52] U.S. Cl. ...................................... 502/242
[58] Field of Search ......................... 502/242

[56] References Cited

U.S. PATENT DOCUMENTS

| | | | |
|---|---|---|---|
| 3,914,383 | 10/1975 | Kirsch et al. | 423/328 |
| 4,367,163 | 1/1983 | Pinnavaia et al. | 252/455 |
| 4,510,257 | 4/1985 | Lewis et al. | 502/63 |
| 4,600,503 | 7/1986 | Angevine et al. | 208/251 |
| 4,613,584 | 9/1986 | Schneider et al. | 502/304 |
| 4,629,713 | 12/1986 | Suzuki et al. | 502/84 |
| 4,701,428 | 10/1987 | Bellussi et al. | 502/242 |
| 4,728,439 | 3/1988 | Kirker et al. | 502/242 |
| 4,831,005 | 5/1989 | Aufdembrink | 502/242 |
| 4,831,006 | 5/1989 | Aufdembrink | 502/242 |
| 4,859,648 | 8/1989 | Landis et al. | 502/242 |
| 4,902,392 | 2/1990 | Aufdembrink et al. | 208/110 |
| 4,933,310 | 6/1990 | Aufdembrink et al. | 502/71 |

FOREIGN PATENT DOCUMENTS

| | | |
|---|---|---|
| 0131685 | 3/1984 | Fed. Rep. of Germany . |
| 0205711 | 12/1985 | United Kingdom . |
| 8701444 | 4/1989 | United Kingdom . |

OTHER PUBLICATIONS

Journal of Solid State Chemistry 66, 1987, pp. 7-10.
Journal of Solid State Chemistry 49, 1983, pp. 300-308.
"A New Class of Compound . . . ", A. F. Reid et al., 1967, pp. 1228-1233.
Angew. Chem. Nr. 12, 1960, pp. 413-415 (no translation).

*Primary Examiner*—Carl F. Dees
*Attorney, Agent, or Firm*—Alexander J. McKillop; Charles J. Speciale; Laurence P. Hobbes

[57] ABSTRACT

A layered product comprises a layered metal oxide and pillars of an oxide of at least one element selected from Groups IB, IIB, IIIA, IIIB, IVA, IVB, VA, VB, VIA, VIIA and VIIIA of the Periodic Table of the Elements separating the layers of the metal oxide. Each layer of the metal oxide has the general formula $$[M_x\square_y Z_{2-(x+y)}O_4]^{q-}$$

wherein M is at least one metal of valence n wherein n is an integer between 0 and 7, $\square$ represents a vacancy site, Z is a tetravalent metal, and wherein $$q = 4y - x(n-4)$$

$$0 < x+y < 2$$

11 Claims, 1 Drawing Sheet

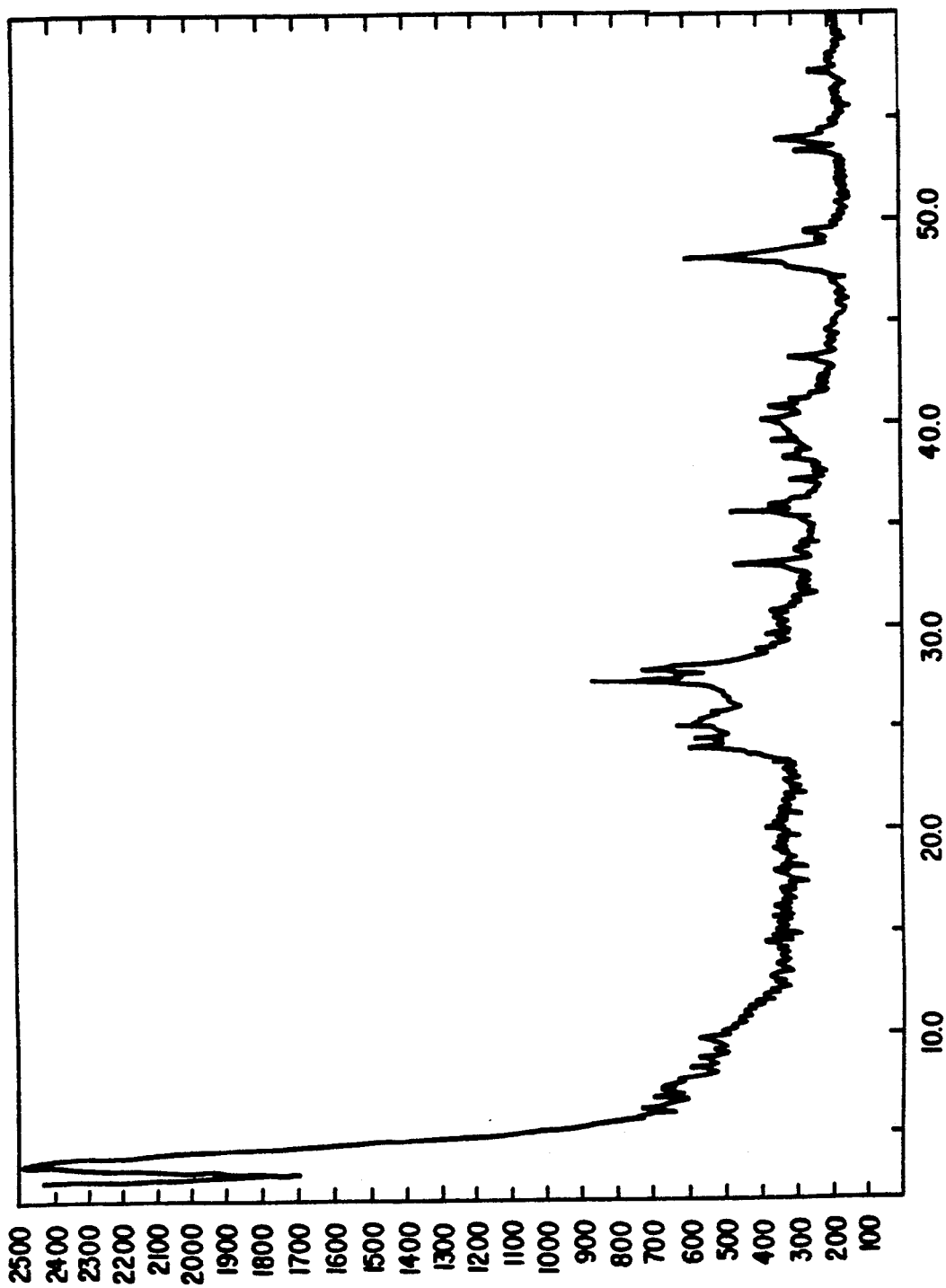

LAYERED METAL OXIDES CONTAINING INTERLAYER OXIDES AND THEIR SYNTHESIS

This is a continuation of copending application Ser. No. 443,071, filed on Oct. 5, 1989 and now abandoned which is a continuation of copending application Ser. No. 179,949, filed on Feb. 25, 1988 and now abandoned.

The present invention relates to layered metal oxides containing interlayer polymeric oxides as well as a method for preparing the same.

Many layered materials are known which have three-dimensional structures which exhibit their strongest chemical bonding in only two dimensions. In such materials, the stronger chemical bonds are formed in two-dimensional planes and a three-dimensional solid is formed by stacking such planes on top of each other, the interactions between the planes being weaker than the chemical bonds holding an individual plane together. The weaker bonds generally arise from interlayer attractions such as Van der Waals forces, electrostatic interactions, and hydrogen bonding. In those situations where the layered structure has electronically neutral sheets interacting with each other solely through Van der Waals forces, a high degree of lubricity is manifested as the planes slide across each other without encountering the energy barriers that arise with strong interlayer bonding. Graphite is an example of such a material. The silicate layers of a number of clay materials are held together by electrostatic attraction provided by ions located between the layers. In addition, hydrogen bonding interactions can occur directly between complementary sites on adjacent layers, or can be provided by interlamellar bridging molecules.

Laminated materials such as clays may be modified to increase their surface area. In particular, the distance between the layers can be increased substantially by absorption of various swelling agents such as water, ethylene glycol, amines, and ketones, which enter the interlamellar space and push the layers apart. However, the interlamellar spaces of such layered materials tend to collapse when the molecules occupying the space are removed by, for example, exposing the clays to high temperatures. Accordingly, such layered materials having enhanced surface area are not suited for use in chemical processes involving even moderately severe conditions.

The extent of interlayer separation can be estimated by using standard techniques such as X-ray diffraction to determine the basal spacing, also known as "repeat distance" or "d-spacing". These values indicate the distance between, for example, the uppermost margin of one layer with the uppermost margin of its adjoining layer. If the layer thickness is known, the interlayer spacing can be determined by subtracting the layer thickness from the basal spacing.

Various approaches have been taken to provide layered materials of enhanced interlayer distance having thermal stability. Most techniques rely upon the introduction of an inorganic "pillaring" agent between the layers of a layered material. For example, U.S. Pat. No. 4,216,188 discloses a clay which is cross-linked with metal hydroxide prepared from a highly dilute colloidal solution containing fully separated unit layers and a cross-linking agent comprising a colloidal metal hydroxide solution. However, this method requires a highly dilute forming solution of the clay (less than 1 g/l) in order to effect full layer separation prior to incorporation of the pillaring species, as well as positively charged species of cross linking agents.

U.S. Pat. No. 4,248,739 relates to stable pillared interlayered clay prepared from smectite clays reacted with cationic metal complexes of metals such as aluminum and zirconium. The resulting products exhibit high interlayer separation and thermal stability.

U.S. Pat. No. 4,176,090, incorporated herein by reference, discloses a clay composition interlayered with polymeric cationic hydroxy metal complexes of metals such as aluminum, zirconium and titanium. Interlayer distances of up to 16 Angstrom are claimed although only distances restricted to about 9 Angstrom are exemplified for calcined samples. These distances are essentially unvariable and related to the specific size of the hydroxy metal complex.

Silicon-containing materials are believed to be a highly desirable species of pillaring agent owing to their high thermal stability characteristics. U.S. Pat. No. 4,367,163, describes a clay intercalated with silica prepared by impregnating a clay substrate with a silicon-containing reactant such as an ionic silicon complex, e.g., silicon acetylacetonate, or a neutral species such as $SiCl_4$. The clay may be swelled prior to or during silicon impregnation with a suitable polar solvent such as methylene chloride, acetone, benzaldehyde, tri- or tetraalkylammonium ions, or dimethylsulfoxide. This method, however, appears to provide only a monolayer of intercalated silica resulting in a product of small spacing between layers, about 2-3 Angstrom as determined by X-ray diffraction.

In one aspect, the present invention resides in a layered product comprising a layered metal oxide and pillars of an oxide of at least one element selected from Groups IB, IIB, IIIA, IIIB, IVA, IVB, VA, VB, VIA, VIIA and VIIIA of the Periodic Table of the Elements (Fisher Scientific Co. Cat. No. 5-702-10, 1978) separating the layers of the metal oxide, wherein each layer of the metal oxide has the general formula

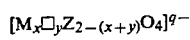

$$[M_x\square_yZ_{2-(x+y)}O_4]^{q-}$$

wherein M is at least one metal of valence n wherein n is an integer between 0 and 7 and preferably is 2 or 3, $\square$ represents a vacancy site, Z is a tetravalent metal, preferably titanium, and wherein $q = 4y - x(n-4)$ and preferably is 0.6–0.9, $0 < x + y < 2$ In another aspect, the present invention relates to a method for preparing the layered product described in the preceding paragraph which method comprises the steps of starting with said layered metal oxide and physically separating the layers thereof by introducing an organic cationic species between the layers at interlayer anionic sites associated with the layered oxide, introducing between the separated layers of the layered oxide a compound capable of conversion to an oxide and then converting said compound to the oxide to form oxide pillars separating adjacent layers of the layered oxide.

It is to be appreciated that the term "layered" metal oxide is used herein in its commonly accepted sense to refer to a material which comprises a plurality of separate metal oxide layers which are capable of being physically displaced away from one another such that the spacing between adjacent layers is increased. Such displacement can be measured by X-ray diffraction techniques and/or by density measurements.

The present invention is particularly useful in that it permits the preparation of pillared oxide products of relatively high interplanar distance (d-spacing), e.g., greater than about 10 Angstrom and preferably greater than 20 Angstrom up to and even exceeding 30 Angstrom. These materials are capable of being exposed to severe conditions such as those encountered in calcining, e.g., at temperatures of about 450° C. for about two or more hours, e.g., four hours, in nitrogen or air, without significant decrease, say, e.g., less than about 10%, in interlayer distance. Furthermore, such pillared oxides can be prepared without the severe dilution often necessary to introduce the interspathic material in prior art techniques of interlayering. Finally, the size of interspathic oxide contained within the final product can be greatly varied because the oxide precursor species is introduced in an electrically neutral form such that the amount of interspathic material incorporated within the layered titanometallate is not dependent upon the charge density of the original layered oxide. Charge density should be taken into consideration in determining the suitability of the cationic species introduced between the layers in the procedure used to prop open the layers prior to pillaring.

The present invention utilizes a layered metal oxide, preferably a titanometallate starting material which contains anionic sites having interspathic cations associated therewith. Such interspathic cations may include hydrogen ion, hydronium ion and alkali metal cation.

More specifically, the present invention employs a layered metal oxide starting material in which each layer has the general formula $$[M_x\square_y Z_{2-(x+y)}O_4]^{q-}$$

wherein M is at least one metal of valence n wherein n is an integer between 0 and 7 and preferably is 2 or 3, $\square$ represents a vacancy site, Z is a tetravalent metal, preferably titanium, and wherein $$q = 4y - x(n-4) \text{ and preferably is } 0.6-0.9,$$

$$0 < x + y < 2$$

Interposed between the layers of the oxide will be charge-balancing cations A of charge m wherein m is an integer between 1 and 3, preferably 1. Preferably A is a large alkali metal cation selected from the group consisting of Cs, Rb and K and M is a divalent or trivalent metal cation selected from at least one Mg, Sc, Mn, Fe, Cr, Ni, Cu, Zn, In, Ga and Al. For example, M can be both In and Ga. Structurally, these metal oxides consist of layers of $(M_x\square_y Z_{1-x-y})O_6$ octahedra which are *trans* edge-shared in one dimension and *cis* edge-shared in the second dimension forming double octahedral layers which are separated by the A cations in the third dimension. In the preferred example in which Z is titanium, these materials can be prepared by high temperature fusion of a mixture of 1) metal oxide, 2) alkali metal carbonate or nitrate and 3) titanium dioxide; or by fusion of a mixture of alkali metallate and titanium dioxide. Such fusion can be carried out in air in ceramic crucibles at temperatures ranging between 600° to 1100° C. after the reagents have been ground to an homogeneous mixture. The resulting product is ground to 20 to 250 mesh, preferably about 100 mesh, prior to the organic swelling and polymeric oxide intercalation steps.

Further description of the layered titanometallate starting materials and their methods of preparation can be found in the following references:

Reid, A. F.; Mumme, W. G.; Wadsley, A. D. *Acta Cryst.* (1968), B24, 1228; Groult, D.; Mercy, C.; Raveau, B. *J. Solid State Chem.* 1980, 32 289; England, W. A.; Burkett, J. E.; Goodenough; J. B., Wiseman, P. J. *J. Solid State Chem.* 1983, 49 300.

Use of these layered metal oxides as the layered starting material of the present invention permits inclusion of different metal atoms into the layered starting material being treated which allows potential catalytically active sites to be incorporated in the stable layer itself. Moreover, variable amounts of metal atoms may be added to provide a catalyst with optimum activity for a particular process. Furthermore, the infinite trans-edge shared layer structure of the titanometallates instead of the sheared 3-block structure of, for example, $Na_2Ti_3O_7$ may reduce or eliminate shearing of the layers as a possible mechanism for thermal or hydrothermal decomposition of the calcined intercalated material. These titanometallate materials may possess even greater thermal stability than silicotitanate molecular sieves. In addition, the variable charge density on the oxide layer possible for these layered metal oxides due to the various oxidation states of metal oxides the incorporated metal atom and the varying stoichiometry of the materials may allow variation in the amount of the organic cationic species which can be exchanged into the material. This, in turn, permits variation of the ultimate concentration of the oxide pillars between the layers of the final product.

In the method of the invention the layered metal oxide starting material is initially treated with a "propping" agent comprising a source of organic cation, such as organoammonium cation, in order to effect an exchange of the interspathic cations resulting in the layers of the starting material being propped apart. Suitable organoammonium cations include such as n-dodecylammonium, octylammonium, n-heptylammonium, n-hexylammonium and n-propylammonium. During this propping or swelling step it is important to maintain a low hydrogen ion concentration to prevent decomposition of the titanometallate structure as well as to prevent preferential sorption of hydrogen ion over the propping agent. A pH range of 6 to 10, preferably 7 to 8.5 is generally employed during treatment with the propping agent. After this treatment, it has been found advantageous to wash out excess propping agent using a propping agent-soluble reagent followed by washing with water. For example, ethanol is soluble in and hence suitable for use with an n-octylamine propping agent. Such washing permits greater incorporation of the oxide pillar precursor in the layered metal oxide. The water treatment allows penetration of water into the interlayer spaces treatment which assists in subsequent hydrolysis the oxide pillar precursor.

The foregoing treatment results in the formation of a layered metal oxide of enhanced interlayer separation depending upon the size of the organic cation introduced. In one embodiment, a series of organic cation exchanges can be carried out. For example, an organic cation may be exchanged with an organic cation of greater size, thus increasing the interlayer separation in a step-wise fashion. Preferably, contact of the layered oxide with the propping agent is conducted in aqueous medium so that water is trapped between the layers of the "propped" species.

After the ion exchange, the organic-"propped" species is treated with a compound capable of conversion, preferably by hydrolysis, to pillars of an oxide, preferably to a polymeric oxide. Where the treatment involves hydrolysis, this may be carried out using the water already present in organic-"propped" material. In this case, the extent of hydrolysis may be modified by varying the extent to which the organic-"propped" species is dried prior to addition of the polymeric oxide precursor.

It is preferred that the organic cation deposited between the layers be capable of being removed from the pillared material without substantial disturbance or removal of the interspathic polymeric oxide. For example, organic cations such as n-octylammonium may be removed by exposure to elevated temperatures, e.g., calcination, in nitrogen or air, or by chemical oxidation preferably after the interspathic polymeric oxide precursor has been converted to the polymeric oxide pillars in order to form the layered product of the present invention.

The products of the present invention, especially when calcined, exhibit high surface area, e.g., greater than 200, 300, 400 or even 600 m$^2$/g, and thermal and hydrothermal stability making them highly useful as catalysts or catalytic supports, for hydrocarbon conversion processes for example, cracking and hydrocracking.

According to the method of the invention, the layered metal oxide starting material is initially subjected to a swelling or propping step in which the material is treated with an organic compound capable of forming cationic species such as organophosphonium or organoammonium ion, between the oxide layers. Insertion of the organic cation between the adjoining layers serves to physically separate the layers in such a way as to make the layered material receptive to the interlayer addition of an electrically neutral, hydrolyzable, polymeric oxide precursor. In particular, alkylammonium cations have been found useful in the present invention. Thus $C_3$ and larger alkylammonium, e.g., n-octylammonium, cations are readily incorporated within the interlayer spaces of the layered metal oxide serving to prop open the layers in such a way as to allow incorporation of the polymeric oxide precursor. The extent of the interlayer spacing can be controlled by the size of the organoammonium ion employed so that use of the n-propylammonium can achieve a interlayer spacing of 2 to 5 Angstrom whereas to achieve an interlayer spacing of 10 to 20 Angstrom an n-octylammonium cation or a cation of equivalent length is required. Indeed, the size and shape of the organic cation can affect whether or not it can be incorporated within the layered structure at all. For example, bulky cations such as tetrapropylammonium are generally undesirable for use in the present method while n-alkyl ammonium cations such as those derived from n-alkyl primary amines and $R_3R'N^+$ cations where R is methyl or ethyl and R is an n-alkyl group with at least 5 carbon atoms, are preferred. Preferably treatment with the organic cationic species is conducted in aqueous media so that water is then available to hydrolyze the electrically neutral, hydrolyzable polymeric chalcogenide precursor subsequently introduced into the "propped" product.

Interpathic oxide pillars are then formed between the layers of the propped or swollen metal oxide starting material and may include an oxide, preferably a polymeric oxide, of zirconium or titanium or more preferably of an element selected from Group IVB of the Periodic Table (Fischer Scientific Company Cat. No. 5-702-10, 1978), other than carbon, i.e., silicon, germanium, tin and lead. Other suitable oxides include those of Group VA, e.g., V, Nb, and Ta, those of Group IIA, e.g., Mg or those of Group IIIB, e.g., B. Most preferably, the pillars include polymeric silica. In addition, the oxide pillars may include an element which provides catalytically active acid sites in the pillars, preferably aluminum.

The oxide pillars are formed from a precursor material which is preferably introduced between the layers of the organic "propped" species as a cationic, or more preferably, electrically neutral, hydrolyzable compound of the desired elements, e.g., those of Group IVB. The precursor material is preferably an organometallic compound which is a liquid under ambient conditions. In particular, hydrolyzable compounds, e.g., alkoxides, of the desired elements of the pillars are utilized as the precursors. Suitable polymeric silica precursor materials include tetraalkylsilicates, e.g., tetrapropylorthosilicate, tetramethylorthosilicate and, most preferably, tetraethylorthosilicate. Where the pillars are also required to include polymeric alumina, a hydrolyzable aluminum compound can be contacted with the organic "propped" species before, after or simultaneously with the contacting of the propped titanometallate with the silicon compound. Preferably, the hydrolyzable aluminum compound employed is an aluminum alkoxide, e.g., aluminum isopropoxide. If the pillars are to include titania, a hydrolyzable titanium compound such as titanium alkoxide, e.g., titanium isopropoxide, may be used. In addition, the oxide precursor may contain zeolite precursors such that exposure to conversion conditions results in the formation of interspathic zeolite material as at least part of the oxide pillars.

After hydrolysis to produce the oxide pillars and calcination to remove the organic propping agent, the final pillared product may contain residual exchangeable cations. Such residual cations in the layered material can be ion exchanged by known methods with other cationic species to provide or alter the catalytic activity of the pillared product. Suitable replacement cations include cesium, cerium, cobalt, nickel, copper, zionc, manganese, platinum, lanthanum, aluminum, ammonium, hydronium and mixtures thereof.

The resulting pillared products exhibit thermal stability at temperatures of 500° C. or even higher as well as substantial sorption capacities (as much as 10 to 25 wt % for $H_2O$ and $C_6$ hydrocarbon). Silica-pillared products possess interlayer separations of greater than 12A and surface areas greater than 250 m$^2$/g when divalent metal atoms, e.g., Mg, Ni, Cu and Zn, are present as the metal M of the product. Silica-pillared products incorporating trivalent metal atoms, e.g., Sc, Mn, Fe, Cr, In, Ga and Al can possess interlayer separations of 6 to 15 A. The calcined products of the present invention, particularly those containing interspathic polymeric oxides as prepared by the method of the present invention are suited to use as catalysts for petroleum processing owing to their high surface areas, large interlayer openings, thermal stability and the wide variety of metal atoms which may be incorporated therein.

When used as a catalyst, it may be desirable to incorporate the pillared product of the invention with another material, i.e. a matrix, resistant to the temperatures and other condition employed in organic conversion processes. Such materials include active and inactive materials and synthetic or naturally occurring zeolites as well as inorganic materials such as clays, silica and/or metal oxide. Use of a matrix in conjunction with the pillared product, i.e. combined therewith, which is active, tends to improve the conversion and/or selectivity of the catalyst in certain organic conversion processes. Inactive materials suitably serve as diluents to control the amount of conversion in a given process so that products can be obtained economically without employing other means for controlling the rate of reaction. These materials may be incorporated into naturally occurring clays, e.g. bentonite and kaolin, to improve crush strength of the catalyst under commercial operating conditions. Said materials, i.e. clays, oxides, etc., function as binders for the catalyst. It is desirable to provide a catalyst having good crush strength because in commercial use it is desirable to prevent the catalyst from breaking down into powder-like materials. These clay binders have been employed normally only for the purpose of improving the crush strength of the catalyst.

Naturally occurring clays which can be composited with the pillared product include montmorillonite and kaolin families which include the subbentonites, and the kaolins commonly known as Dixie, McNamee, Georgia and Florida clays or others in which the main mineral constitutent is halloysite, kaolinite, dickite, nacrite, or anauxite. Such clays can be used in the raw state as originally mined or initially subjected to calcination, acid treatment or chemical modification. Matrix materials useful for compositing with the pillared product also include inorganic oxides, notably alumina or silica.

In addition to the foregoing materials, the pillared product of the invention can be composited with a porous matrix material such as aluminum phosphate, silica-alumina, silica-magnesia, silica-zirconia, silic-thoria, silica-beryllia, silica-titania as well as ternary compositions such as silica-alumina-thoria, silica-alumina-zirconia, silica-alumina-magnesia and silica-magnesia-zirconia. The relative proportions of finely divided pillared product and inorganic oxide gel matrix vary widely, with the content of the pillared product ranging from 1 to 90 percent by weight and more usually, particularly when the composite is prepared in the form of beads or extrudates, in the range of 2 to 80 weight percent of the composite.

The present invention is illustrated further by the following Examples and the accompanying drawing which provides the X-ray diffraction pattern of a pillared titanometallate of Example 3. In these examples, X-ray diffraction data were obtained by standard techniques using K-alpha doublet of copper radiation.

EXAMPLE 1

Preparation of Layered Titanometallates $CsNO_3$ (53.62 g, 0.2751 mole), $Ni(NO_3)_2 \cdot 6H_2O$ (40.00 g, 0.1375 mole), and $TiO_2$ (51.81 g, 0.6482 mole) were ground to a homogenous mixture. The solids were heated in air to 420° C. for three hours followed by firing at 1000° C. for 12 hours. An x-ray powder pattern of the product agreed with the literature reported for the isostructural compound, $Rb_{0.7}(Mn_{0.7}Ti_{1.3})O_4$ given by Reid, et al. Id. (Interlayer distance = 8.41 Å).

The materials set out in Table 1 were also synthesized by fusion of a metal oxide source, alkali carbonate or nitrate and $TiO_2$; or an alkali metallate and $TiO_2$.

TABLE 1

| Reagent Stoichiometry | Source Of Metal Oxide | Fusion Temp., °C. | Lowest X-Ray Line. 2 Theta | d (Å) |
| --- | --- | --- | --- | --- |
| $Cs_{0.7}(Mn_{0.7}Ti_{1.3})O_4$ | $CsMnO_4$ | 1000 | 10.3 | 8.57 |
| $Cs_{0.7}(Sc_{0.7}Ti_{1.3})O_4$ | $Sc_2O_3$ | 1000 | 10.3 | 8.57 |
| $Cs_{0.7}(Mg_{0.35}Ti_{1.65})O_4$ | $MgO$ | 1000 | 10.3 | 8.57 |
| $Rb_{0.7}(Mn_{0.7}Ti_{1.3})O_4$ | $RbMnO_4$ | 900 | 11.10 | 7.97 |
| $K_{0.8}(Ni_{0.4}Ti_{1.6})O_4$ | $Ni(NO_3)_2$ | 1050 | 11.4 | 7.76 |
| $K_{0.8}(Cu_{0.4}Ti_{1.6})O_4$ | $Cu(OH)_2$ | 1050 | 11.3 | 7.83 |

TABLE 2

| | Preparation of Layered Titanometallate | | | |
| --- | --- | --- | --- | --- |
| Reagent stoichiometry | Reagents | Rxn Conditions[a] | Product analysis | d (Å)[b] |
| $Cs_{0.70}(Ni_{0.35}Ti_{1.65})O_4$ | $Cs_2CO_3$, $Ni(NO_3)_2$, $TiO_2$ | 420° C., 200 min 1000° C., 720 min | $Cs_{0.57}(Ni_{0.32}Ti_{1.70})O_4$ | 8.41 |
| $K_{0.80}(Zn_{0.40}Ti_{1.60})O_4$ | $K_2CO_3$, ZnO $TiO_2$ | 900° C., 200 min 1050° C. 720 min regrind, refire | $K_{0.66}(Zn_{0.35}Ti_{1.49})O_4$ | 7.83 |
| $K_{0.80}(Mg_{0.40}Ti_{1.60})O_4$ | $K_2CO_3$, MgO $TiO_2$ | 900° C., 200 min 1000° C., 720 min regrind, refire | $K_{0.73}(Mg_{0.39}Ti_{1.62})O_4$ | 7.83 |
| $K_{0.80}(Mn_{0.80}Ti_{1.20})O_4$ | $KMnO_4$, $TiO_2$ | 920° C., 600 min 1100° C., 720 min | $K_{0.69}(Mn_{0.79}Ti_{1.23})O_4$ | 7.76 |
| $K_{0.80}(Fe_{0.80}Ti_{1.20})O_4$ | $K_2CO_3$, $Fe_2O_3$ $TiO_2$ | 900° C., 200 min 1000° C., 720 min | $K_{0.69}(Fe_{0.73}Ti_{1.28})O_4$ | 7.90 |
| $Cs_{0.70}(Al_{0.70}Ti_{1.30})O_4$ | $Cs_2CO_3$, $Al_2O_3$ $TiO_2$ | 420° C., 180 min 1000° C., 720 min | $Cs_{0.72}(Al_{0.53}Ti_{1.42})O_4$ | 8.84 |

[a] All firings were carried out in air.
[b] d-layer spacing from x-ray powder diffraction data.

Additional layered titanometallates were prepared. Reagents, reagent stoichiometries, reaction temperatures, and dwell times are displayed in Table 2 below. The reactions were carried out by thoroughly grinding the reagents to homogenous mixtures and firing in ceramic crucibles. In cases where potassium was used as the alkali metal cation, regrinding and refiring was required to obtain the layered phase in reasonable purity for further reactions. The stiff powders obtained were ground to roughly 100 mesh before further reactions.

EXAMPLE 2

Propping Layered Titanometallate By Ion Exchange With Octylammonium Chloride The interlayer openings in the materials prepared in Example 1 were propped by exchange of the alkali metal cations with octylammonium ion. Excess octylamine (5 mole equiv/mole equiv of layered metal oxide) was slowly added to a solution of 12% HCl (4.9 equiv HCl/mole layered metal oxide) while keeping the temperature of the reaction mixture below 50° C. The layered titanometallate was then added to the octylammonium chloride solution and the mixture was heated to reflux for 24 hours.

The reaction mixture was cooled, filtered, and washed with hot distilled $H_2O$ (1.5 times the volume of the reaction solution). The solid was air dried at room temperature. Table 3 below sets out the composition and the d-spacings of the lowest two theta peak in the X-ray diffraction pattern of the propped materials.

TABLE 3

Composition of n-Octylammonium-Exchanged Titanomettallates

| Composition[a,b] | % N | d (A)[c] |
|---|---|---|
| $H_3O^+{}_{0.34}Cs_{0.22}(NH_3R^+)_{0.16}[Mg_{0.35}Ti_{1.76}]O_4$ | 0.98 | 25.2 |
| $H_3O^+{}_{0.30}Rb_{0.07}(NH_3R^+)_{0.43}[Mn_{0.79}Ti_{1.39}]O_4$ | 2.24 | 24.5 |
| $H_3O^+{}_{0.43}Cs_{0.23}(NH_3R^+)_{0.10}[Mn_{0.76}Ti_{1.37}]O_4$ | 0.60 | 23.2 |
| $H_3O^+{}_{0.33}Cs_{0.12}(NH_3R^+)_{0.21}[Al_{0.66}Ti_{1.38}]O_4$ | 1.25 | 24.5 |
| $H_3O^+{}_{0.11}Cs_{0.14}(NH_3R^+)_{0.44}[Ni_{0.35}Ti_{1.75}]O_4$ | 2.40 | 23.9 |
| $H_3O^+{}_{0.39}K_{0.15}(NH_3R^+)_{0.37}[Mg_{0.35}Ti_{1.69}]O_4$ | 2.04 | 25.2 |
| $H_3O^+{}_{0.33}K_{0.03}(NH_3R^+)_{0.56}[Zn_{0.46}Ti_{1.75}]O_4$ | 2.68 | 24.6 |
| $H_3O^+{}_{0.15}K_{0.19}(NH_3R^+)_{0.43}[Fe_{0.78}Ti_{1.39}]O_4$ | 2.31 | 24.5 |
| $H_3O^+{}_{0.31}K_{0.17}(NH_3R^+)_{0.34}[Mn_{0.82}Ti_{1.30}]O_4$ | 1.97 | 24.8 |

[a]$R = C_8H_{17}$
[b]$H_3O+$ content was determined by subtracting Cs and $NH_3R$ content from the total charge required to balance the negative charge of the metal-titanium layer.
[c]d-layer spacing from lowest two theta peak in x-ray diffraction pattern.

EXAMPLE 3

Treatment Of Swelled Titanometallates With Tetraethylorthosilicate

The octylammonium-exchanged solids of Example 2 were then stirred in EtOH for 2 hours, filtered, and air dried at room temperature for 2 hours. The solids were then slurried with $H_2O$ using a blender to ensure maximum mixing of the hydrophobic solid with water. The slurry was then transferred to a beaker and stirred overnight. The mixture was filtered and air dried for 4 hours.

The resulting filter cake was treated with tetraethylorthosilicate (TEOS) (5 g TEOS/g solid) for 72 hours. The pillared material was obtained by filtering this slurry and drying the solid in air. Calcination of the pillared material at 500° C. for about 4 hours in air eliminated octylamine and produced the molecular sieve. Analysis of the materials thus treated are set out in Table 4 below. The X-ray diffraction pattern of the pillared $Cs_{0.57}(Ni_{0.32}Ti_{1.70})O_4$ material is set out in the drawing.

TABLE 4

Titanometallates Containing Interspathic Polymeric Silica

| M | Starting Layered Titanometallate | Interlayer Opening (A)[a] | % metal | % $SiO_2$ | Residual[d] Cation A (%) |
|---|---|---|---|---|---|
| Ni | $Cs_{0.57}(Ni_{0.32}Ti_{1.70})O_4$ | 15.7 | 7.2 | 23.2 | 7.1 |
| Mg | $K_{0.73}(Mg_{0.39}Ti_{1.62})O_4$ | 14.9 | 5.2 | — | 2.9 |
| Zn | $K_{0.66}(Zn_{0.35}Ti_{1.49})O_4$ | 14.6 | 12.9 | — | 0.45 |
| Al | $Cs_{0.72}(Al_{0.53}Ti_{1.42})O_4$ | 10.2 | 9.9 | 8.5 | 8.3 |
| Fe | $K_{0.69}(Fe_{0.73}Ti_{1.28})O_4$ | 8.6 | 16.1 | 19.6 | 3.0 |
| Mn | $K_{0.69}(Mn_{0.79}Ti_{1.23})O_4$ | 5.5 | 19.9 | 21.3 | 2.6 |

[a]d spacing from powder diffraction minus thickness of metal oxide layer
[b]A = alkali metal atom content in molecular sieve.

EXAMPLE 4

Pillaring Of Vacancy Titanate

In this example the layered starting material was a titanate having the empirical formula $Cs_{0.7}Ti_{1.82}O_4$. This material contains vacancies at certain titanium sites in the layers and so can be described by the general formula $Cs_{4y}(\square_y Ti_{2-y})O_4$ wherein $\square$ is a vacancy site and y is 0.18.

The layered vacancy titanate was prepared by the high temperature solid state reaction of $Cs_2CO_3$ and $TiO_2$ in the stoichiometry of 1:5.2. The $Cs_2CO_3$ employed was ground to fine powder (less than 100 mesh) dried and stored in a vacuum oven at 180° C. The $TiO_2$ employed was used as received. The solids (50 g $Cs_2CO_3$ and 63.93 g $TiO_2$) were ground to an homogenous mixture which was fired at 650° C. for 10 hours and, after regrinding, was then fired at 950° C. for a further 10 hours. The resultant product was then ground.

30 g of the titanate product was then swollen by replacing with octylamine/HCl (mole ratio 1 titanate: 5 octylamine:4.9 HCl) for 14 hours. After washing with 1000 ml of water, the product was dried in air overnight.

25 g of the swelled titanate was stirred in 300 ml ethanol, filtered and air dried. The dried solid was then slurried in 500 ml water for 24 hours, pillared and air dried overnight. The resultant solid (16.4 g) was stirred with 100 g of TEOS for 24 hours and the mixture was filtered and air dried to yield 18.5 g of solid product. The required porous molecular sieve was obtained by calcining the product in air at 500° C. for 4 hours.

I claim:

1. A layered product comprising a layered metal oxide and pillars of an oxide of at least one element selected from Groups IB, IIB, IIIA, IIIB, IVA, IVB, VA, VB, VIA, VIIA and VIIIA of the Periodic Table of the Elements separating the layers of the metal oxide, wherein each layer of the metal oxide has the general formula

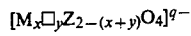

$$[M_x\square_y Z_{2-(x+y)}O_4]^{q-}$$

wherein M is at least one metal of valence n wherein n is an integer between 0 and 7, $\square$ represents a vacancy site, Z is a tetravalent metal, and wherein $$q = 4y - x(n-4)$$

$$0 < x + y < 2$$

2. A product as claimed in claim 1 wherein n is 2 or 3.

3. A product as claimed in claim 1 wherein Z is titanium.

4. A product as claimed in claim 3 wherein y is zero.

5. A product as claimed in claim 1 wherein q is from 0.6-0.9.

6. A product as claimed in claim 1 wherein M is selected from Mg, Sc, Mn, Fe, Cr, Ni, Cu, Zn, In, Ga and/or Al.

7. A product as claimed in claim 1 wherein the pillars comprise polymeric oxide.

8. A product as claimed in claim 1 wherein the pillars comprise polymeric silica.

9. A method for preparing a layered product as claimed in claim 1 comprising the steps of physically separating the layers of the metal oxide by introducing an organic cationic species between the layers at interlayer anionic sites associated with the layered metal oxide, introducing between the separated layers of the metal oxide a compound capable of conversion to an oxide and then converting said compound to the oxide to form oxide pillars separating adjacent layers of the layered metal oxide.

10. A method as claimed in claim 9 wherein the organic species is an alkylammonium cation.

11. A catalyst composition comprising a layered product as claimed in claim 1 and a matrix material.

* * * * *